United States Patent

Van Beeck

[11] 4,226,538
[45] Oct. 7, 1980

[54] DEVICE FOR DETECTING IRREGULARITIES IN A MOVING SHEET MATERIAL

[75] Inventor: Walter P. Van Beeck, Sinaai, Belgium

[73] Assignee: AGFA-GEVAERT N.V., Mortsel, Belgium

[21] Appl. No.: 920,196

[22] Filed: Jun. 29, 1978

[30] Foreign Application Priority Data

Jul. 1, 1977 [GB] United Kingdom ............... 27672/77

[51] Int. Cl.² ............................................ G01N 21/32
[52] U.S. Cl. ..................................... 356/430; 250/572
[58] Field of Search ................ 250/571, 572; 356/429, 356/430, 431, 375

[56] References Cited

U.S. PATENT DOCUMENTS

| | | | |
|---|---|---|---|
| 3,206,606 | 9/1965 | Burgo et al. | 356/430 |
| 3,740,152 | 6/1973 | Iisuka | 356/375 |
| 3,859,538 | 1/1975 | Mannonen | 356/430 |

Primary Examiner—John K. Corbin
Assistant Examiner—Richard Rosenberger
Attorney, Agent, or Firm—William J. Daniel

[57] ABSTRACT

Device and method for the optical inspection of specklike and streaklike defects in a moving web.

A source of radiation illuminates a transverse zone of the web, a series of photocells measures the radiation after transmission through, or reflection from the web, and a grating arrangement modulates the radiation received by the photocells, thereby to modulate the output signal of each cell by an A.C. component.

11 Claims, 8 Drawing Figures

DEVICE FOR DETECTING IRREGULARITIES IN A MOVING SHEET MATERIAL

This invention relates to a device and a method for detecting irregularities in a moving web or sheet material. The invention can be carried out by using a source for directing radiation on the material, and a row of photocells for detecting at distinct lateral or transverse zones of the sheet material variations in the radiation after transmission of the radiation through, or reflection from the said moving sheet material.

Known devices operate satisfactorily for the detection of specklike irregularities since the passage of a speck through the area of radiation of the web introduces a sudden, and hence a relatively high frequency, signal in the output of the corresponding cell. The amplifier circuit for the cell being AC coupled, the signal received by the cell is transmitted and amplified without any substantial deformation.

In the case of streaklike irregularities, however, there is no change in the output signal of a cell as long as the streak is in the beam of radiation. In the absence of any variation, the signal acts electrically as a DC signal which is consequently not amplified in the AC coupled amplifier.

It is possible to detect streaklike irregularities in a moving sheet material by employing DC coupled amplifier circuits for the photocells. However, DC coupling requires complicated and expensive circuitries to ensure stable operation. Furthermore, the source of radiation has to be carefully controlled in order to produce an absolutely constant radiation output in order to maintain a constant DC level of the photocell outputs. For these reasons, the use of DC coupling is hardly ever considered in practice for the present type of inspection devices.

It has been further proposed to bodily oscillate the row of cells lengthwise. The oscillation causes the more or less transmitting and/or reflecting areas produced by a streak to transfer from one cell to the adjacent one. If a streak is several cells wide, the edge of the streak transfers to the next cell. The oscillation of the row of cells causes a modulation of the output signal of each cell by a signal that has a frequency equal to that with which the cells are being oscillated. The described arrangement operates satisfactorily for the detection of streaklike defects but it shows the following disadvantages. The electrical connections of the different photocells to fixed circuits must be flexible to allow the oscillating movement of the row of photocells; suchlike flexible connections require a very careful design and even so, are not reliable over the long time. Further, the oscillating row of cells lack means for strictly equalizing the angular responses of the different cells to one another, hence it may happen that a given zone of the sheet material yields different output signals depending on the particular photocell by which it is being "seen" during the oscillation of the row of cells.

Finally, as a consequence of the non-uniform angular response of a cell, a given area of the sheet material produces an output signal on a given photocell which depends on the particular lateral position taken by the cell during its oscillation or, in other words, the output signal of the cell is within certain limits a function of the angle under which the particular area of the web is "seen" by the cell.

It is the object of the present invention to provide an improved device and method for detecting irregularities or other defects, more in particular streaks, in a moving sheet material, that does not show the disadvantages of the above known device and its use.

It is a further object of the invention to provide a device that may be easily incorporated into existing photoelectric arrangements employed for the detection of specks in running webs, to extend the detection capacity of suchlike devices also to streaks.

It is a still further object of the invention to provide a device the output signal of which may be an FM signal with a relatively large sweep, wherein a limited band of frequencies represents sufficiently accurately the defects to be detected, and wherein the band is situated well above the band wherein the most disturbing noise frequencies, namely from about 10 to 30 Hz, caused by web flutter, are situated.

According to the present invention, a device for detecting speck- and streaklike irregularities in a moving sheet material, comprises a source for directing electromagnetic energy across at least a portion of the width of the material, a row of stationarily mounted radiation responsive photocells that are substantially uniformly spaced transversely across the path of the sheet material to receive radiation from the source after modulation of radiation by the moving sheet material, a grating arrangement disposed in the path of the radiation to such photocells and serving to periodically intercept and transmit radiation from adjacent areas spaced in a direction parallel with the photocell row, and means for displacing the grating arrangement reverse its alternatingly transmission and interception effect, the grating period or spacing being equal to 1/X times the field length of a photocell, X being an integer, and at least equal to 5.

The term "streaklike irregularities" is not limited to defects in the form of so-called pencil lines and the like, but also encompasses defects in the form of stains that can be considered as defects of protracted duration and that in consequence produce DC electric detection signals.

The notion "field length of a photocell" means the length which is obtained by the intersection of the observation field of a photocell and the plane of the grating, said length being measured in said plane in a direction parallel with the row of photocells.

The notion "grating period" means the length of one period of the grating, that is the aggregate length of one radiation transmitting area and one adjacent radiation intercepting area.

The term "sheet material" stands in the present statement for a plurality of distinct sheets that may be fed in spaced or unspaced succession through the device, as well as for webs that may have a length of many hundreds of meters.

The term "modulation of said radiation by the moving sheet material" means both the transmission of the radiation through the web with, the source of radiation and the radiation responsive cells being mounted on opposite sides of the path of the sheet material, and the reflection of the radiation on one surface of the sheet material in case the source of radiation and the cells are mounted on the same side of the path of the sheet material moving through the device.

The following are interesting embodiments of the device according to the invention.

X is greater than 5 and preferably even greater than 10.

The grating arrangement comprises a movable grid that has a plurality of adjacent alternatively radiation intercepting and radiation transmitting areas and that is mounted for limited lateral displacement in its own plane, a stationary grid that has a plurality of openings the position of which corresponds with the position of the photocells so that the grid acts as a diaphragm limiting the angular response of each cell to a whole number of periods of the movable grid, and means for oscillating the movable grid over a distance that is at least equal to one period of the movable grid.

The photocells are arranged for limited displacement in a direction normal to the plane of the stationary grid, thereby to permit the accurate adjustment of the angular response of each cell in correspondance with an even number of areas of said movable grid.

According to the invention, there is also provided a novel method of testing sheet material to detect the presence of defects (e.g. speck and streak-like irregularities) affecting its radiation transmitting or reflecting properties or the site of such defects, which is characterised in that the sheet material is advanced in its own plane across a projected path of radiation which intersects the plane of the sheet material at a zone extending in at least one direction in said plane; alternately intercepting radiation transmitted through or reflected from different portions of each of a number of like incremental sub-zones disposed in succession along said zone of intersection, detecting the resulting transmitted or reflected modulated radiation by a number of photocells each of which has a detection field whose length measured in the direction of said zone direction is a whole number multiple of one of said incremental sub-zones; and deriving AC modulated signals from said cells.

The invention will be described hereinafter by way of example with reference to the accompanying drawings wherein.

Figure 3:
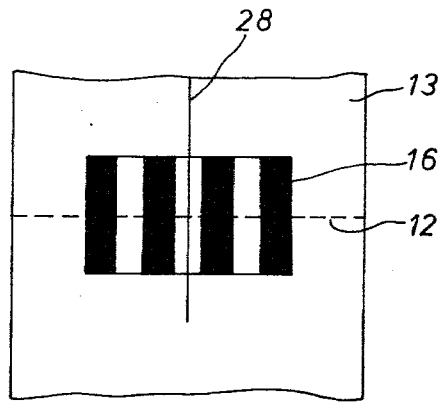
Figure 4:
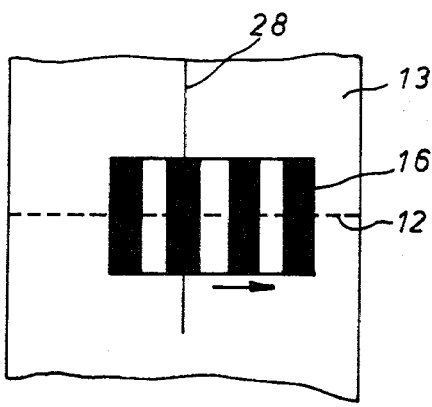
Figure 5:
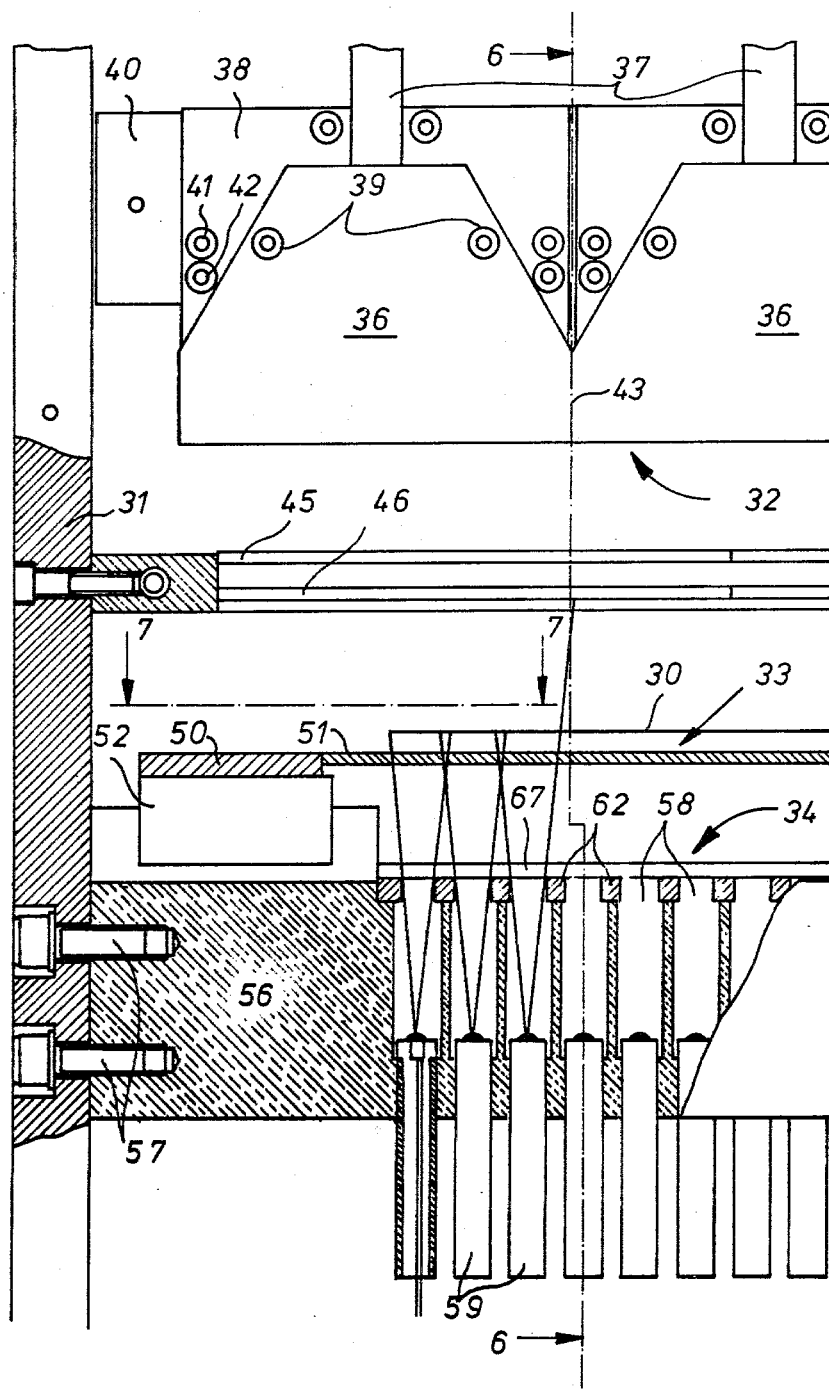
Figure 6:
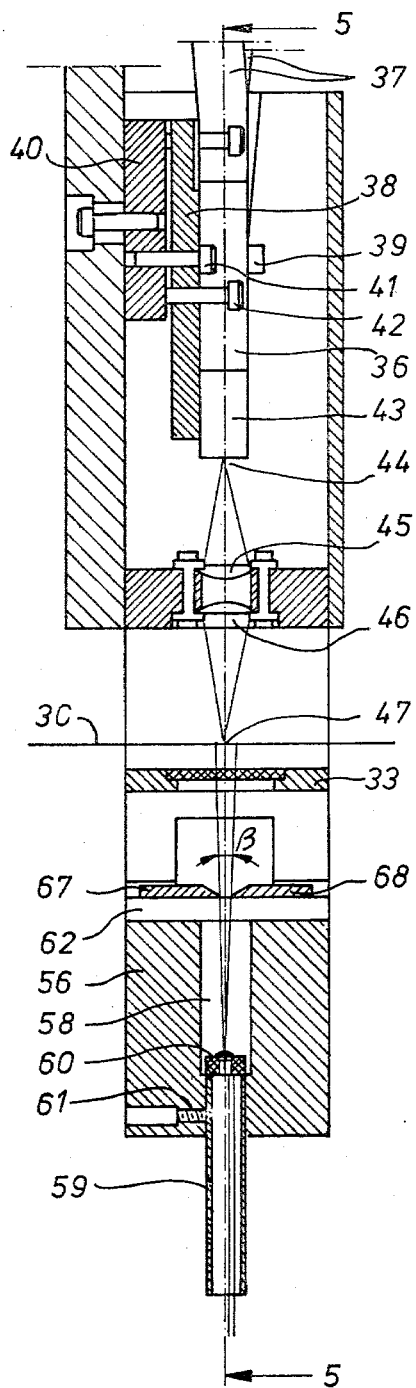
Figure 8:
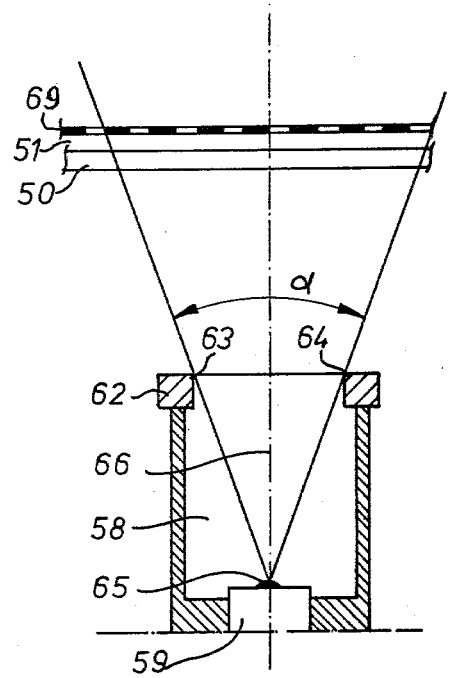
Figure 7:
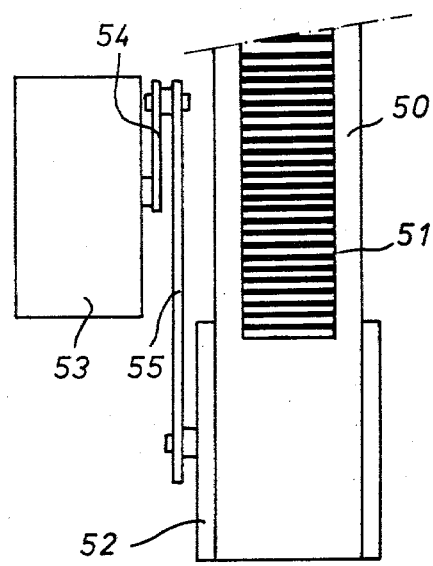

FIG. 3 represents a portion of a film with a streak that moves past a grating in a first position, and FIG. 4 represents the same film portion as in FIG. 3, the grating being displaced over one area to the right, FIG. 5 is a section on line 5—5 of FIG. 6 of the construction of a device according to the present invention, and FIG. 6 is a section on line 6—6 of the device of FIG. 5, FIG. 7 is a plan view of a portion the movable grating of the device of FIGS. 5 and 6 on line 7—7 of FIG. 5, FIG. 8 is an enlarged view of the angular response of a photocell in a plane that is normal and transverse to the film.

Figure 1:
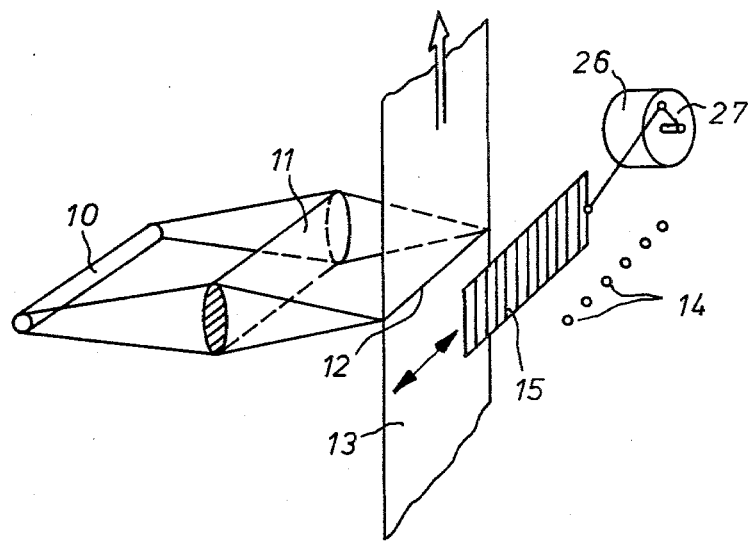
FIG. 1 is a schematic perspective view of the optical arrangement in one embodiment of the present invention.
Figure 2:
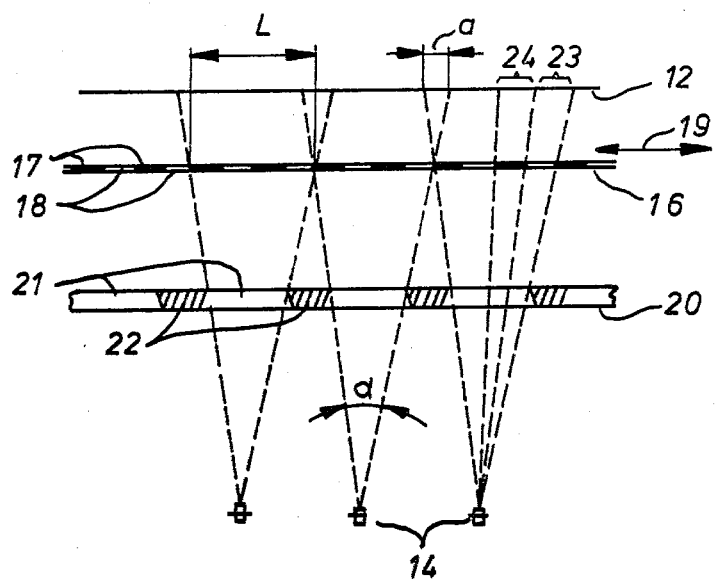
FIG. 2 illustrates the optical arrangement of FIG. 1 considered in a plane normal to that of the film to be inspected and comprising the line of radiation on the film, the source of radiation and the lens being omitted.

Referring to the schematic representation of the optical arrangement of FIGS. 1 and 2, radiation from an elongate source of radiation 10 is focussed by a cylindrical lens 11 to form a transverse line of radiation 12 on a film 13 that is conveyed by means, not shown, to follow a vertically upwardly directed path.

The radiation is attenuated at its passage through the sheet in dependence on the absorption characteristics of said sheet, or of one or more layers coated on said sheet, for said radiation. The line of radiation thus formed at the opposite side of the sheet 13 is analysed by a row of radiation-sensitive photocells 14 that are spaced at equal intervals according to the transverse direction of the sheet.

Between the film 13 and the radiation-sensitive cells 14 there is provided a grating 15 in the path of the radiation towards the cells, which grating is arranged for periodic interception and transmission of radiation at adjacent areas that are spaced in a direction parallel with the photocells and that may have equal widths.

Referring to FIG. 2, said grating consists of a grid 16 that has a plurality of adjacent radiation intercepting areas 17 and radiation transmitting areas 18 and that is mounted for limited displacement in a direction parallel with the film and the row of photocells, as indicated by the arrow 19.

Further, between the movable grid 16 and the photocells 14, there is provided a stationary grid 20 and that radiation transmitting areas 21 and radiation absorbing areas 22. The radiation transmitting areas 21 coincides with the position of the respective photocells, so that in fact said stationary grid 20 forms a diaphragm that defines the observation field for each photocell in a plane that comprises the row of cells 14 and the line of radiation 12. Said observation field of a cell is indicated in FIG. 2 by the angle $\alpha$. It may be seen that said angular response is such that a slight overlapping of the areas "seen" by the cells on the sheet occurs, as indicated by the distance of overlapping a in FIG. 2.

Suchlike slight overlapping may also exist in the plane of the movable grid, but for the sake of simplicity the latter overlapping has not been illustrated in FIG. 2.

In accordance with the invention, the grating period of the grating arrangement is equal to 1/X times the field length of a photocell. Said length is indicated in FIG. 2 by L, and it is thus clear that in the present example X is equal to two since there are two periods of the movable grid 16 covered by each photocell.

It may be seen that the amount of radiation that is received by any photocell is half the amount that would be received in the absence of the grating. This has been schematically indicated in FIG. 2 by a zone 23 of the line of radiation 12 that is transmitted to a cell 14, and a zone 24 of a length equal to that of zone 23 but the radiation of which is intercepted on its path to a cell 14 by an area 17 of the grating.

As the movable grid 16 oscillates in the direction of the arrow 19, for instance actuated by a motor 26 with an arm 27, see FIG. 1, radiation from the zone 23 is alternatingly intercepted by the areas 17 of the grid 16 whereas radiation from the zone 24 is alternatingly transmitted by the areas 18 of the grid 16. The same phenomenon occurs for all the other corresponding zones of the line of radiation 12.

The detection of a streak on the moving film 13 by the described arrangement is illustrated by FIGS. 3 and 4, wherein 13 is a film portion onto which a line of radiation 12, shown in broken lines, is projected from the rearside, 16 is a grating in the form of a movable grid as illustrated in FIGS. 1 and 2 that is disposed slightly above the film portion 13, and the eye of the reader takes in fact the place of a photocell.

The film may be a polyethylene terephthalate support onto which a subbing layer and one or more other layers, for instance light-sensitive photographic layers, may have been coated. The film is considered to be damaged by a streak 28 that is located about centrally of the illustrated film portion and that may have been caused by a sharp edge or the like thereby scraping off the coating of the film while the film was moved along. It is clear that the luminosity of the line of radiation 12 that is produced at the surface of the film facing the eye of the reader will be greater at the place where said line 12 is crossed by the streak 28, since at that place the absorption of the radiation by the several film layers is less than at all the other places of said line 12. If the movable grid 16 is now moved to the right over a distance corresponding with the width of one area of the grid, see FIG. 4, the concerned place of the streak is screened off for the eye. The movement of the grid 16 has thus a modulating effect on the luminosity of each point of the transmitted line of radiation.

The specific signal, when a streak is detected, consists of a FM signal with a large sweep.

The frequency which is obtained when the grating reaches maximum speed is given by $$f_{max} = \frac{2\pi A_0 f X}{L}$$

with
$A_0$: oscillation amplitude of the grating
f: oscillation frequency of the grating
L: field length of a photocell
X: number of grating periods seen by one photocell.
In a practical situation with:
$A_0 = 10$ mm
$f = 5$ Hz
$L = 18$ mm
$X = 18$
$f_{max} = 314$ Hz This means that the oscillation frequency of the grating can be kept relatively low whereby the mechanical actuation of to the moving parts, that increase with the square of the velocity, do not raise particular problems.

This frequency of 314 Hz is not the highest frequency produced upon oscillation since it can be shown, e.g. by Fourier analysis, that much higher frequencies are contained in the sweep of the FM signal. The important advantage, however, of the large sweep is that a relatively wide range of frequencies is available, a given band or bands of which is or are present in greater amplitudes than the other frequencies, so that such more pronounced band or bands contain sufficient information to enable them to be used for measuring whilst the other frequency ranges may be filtered out. This is notably interesting for eliminating frequencies in the range of 10 to 30 Hz that contain in a large amount amplitudes that are caused by web flutter and that may seriously disturb the measuring of streaklike defects that are in fact likewise very low frequency signals.

One embodiment of a device according to the present invention is now described with more constructive details with reference to FIGS. 5 and 6.

Referring to FIG. 5 which represents the left-hand side only of a device for the inspection of a horizontally running film 30, a vertical wall 31 forms one of two laterally spaced supports between which the illumination arrangement 32, the grating 33 and the arrangement 34 of the photocells are mounted.

The illumination arrangement 32 comprises a plurality of adjacent heads 36 each shaped as so-called fish-tail ends of flexible fiber optic conduits such as 37. The conduits 37 have a circular cross-section and terminate in the lower face of the heads 36 in a single row of adjacent fibers. The fiber optic conduits 37 of several heads may be brought together so that their free ends may be illuminated by an appropriate light source, for instance a lamp housing comprising an incandescent lamp. Such lamp housing may further comprise heat filters, spectral filters and cooling means, all as known in the art.

Each head 36 is fitted with pairs of bolts 39 to a square base plate 38. The base plates are adjustably fitted to a common beam 40 by means of three pairs of push and pull screws, such as pull screw 41 and the corresponding push screw 42 illustrated at the left-hand side of FIG. 5. The side-faces 43 of the heads 36 are ground up to the embedded outermost glass fibers so that the arrangement of the heads with their side-faces contacting each other and the careful adjustment of the heads by means of the corresponding adjustment screws, permit the production of an uninterrupted straight line of radiation, indicated in the sectional view of FIG. 6 by the point 44.

The image of the line of radiation is focused on the film 30 by means of two narrow semi-cylindrical lenses 45 and 46 to produce a line of radiation 47 on the film 30. The sharpness of the image of said line 47 on the film depends on the accurate position of the film in the image plane of the lenses 45 and 46, and it will thus be understood that the path of the film through the inspection device requires careful control by means of film supporting rollers mounted close to the inspection device, film tensioning means, and film guiding means, as the case may be. The illumination arrangement 32 described hereinbefore is mounted in a housing that is completely light-tightly constructed, except for the opening for the lenses 45 and 46.

The grating arrangement 33 consists of an elongate rectangular frame 50 of aluminium or the like into the opening of which is cemented a strip 51 of glass provided at its upper surface with a photographic layer that has been exposed and processed to form a grating composed of a multiplicity of transparent and non transparent areas of equal width, as illustrated in FIG. 7. The frame 50 is at both lateral extremities supported by precision linear ball bearings such as the bearing 52 that is diagrammatically illustrated in FIGS. 5 and 7, that permit a linear movement of the grating in a direction parallel with the film and with the row of photocells. The oscillation of the grating in the mentioned direction occurs by means of a small electric motor 53 to which the movable part of one linear bearing is linked by a crank 54 and a connecting rod 55.

The arrangement 34 of the photocells comprises a solid block 56 of light metal that is fixed between the lateral supporting walls 31 by means of screws such as screws 57. The block 56 is provided with a plurality of closely spaced equidistant bores 58 that are arranged in a row which runs parallel with the line of radiation produced on the film. Cylindrical holders 59 provided at their upper extremity with a photocell 60 slidingly fit in the slightly narrowed lower ends of the bores 58, and their axis position may be fixed by means of socket screws such as 61.

The upper side of the block 56 is provided with a plurality of equidistant transverse grooves into which bars 62 with a square cross-section are pressingly fitted. These bars determine with their opposed boundaries 63 and 64, see FIG. 8, together with the position of the sensitive portion 65 of a photocell along the axis 66 of a bore 58, the observation field α of a photocell. In said FIG. 8 there is further illustrated a portion of the grating and for the sake of clearness the thickness of the photographic layer 69 on the glass strip 51, which actually is about 5 micrometers, has been drawn considerably enlarged in order to illustrate the transmitting and intercepting zones that constitute the grating. It is clear that axial adjustment of a cell holder 59 makes it possible to adjust the angular response of the photocell to cover a whole number of periods of the grating, that is to say an equal number of radiation transmitting and radiation absorbing areas. The reason for the slight overlapping of adjacent areas of the film that are being inspected will now be clear, since it is only in that way that the field length of a photocell as defined hereinbefore may be adjusted to correspond with a whole number of periods of the grating, without running the risk that a narrow longitudinal zone of the film would occasionally not be within the observation field of any of two adjacent photocells.

The angular response of a cell in a plane normal to that just described, and also normal to the plane of the film, is not critical at all since in fact it is only necessary for a cell to be capable of viewing the line 47, see FIG. 6. Therefore, and in order to prevent that dispersed radiation could occasionally reach a photocell, the observation field of the cell in the mentioned plane has been reduced to a rather small angle β which is determined by the opposed boundaries of two elongate opaque screens 67 and 68.

In practice, the adjustment of the described device occurs in two steps, the film 30 occupying a stationary position. First the adjustment of the illumination heads 36 as described already hereinbefore is carried out to produce a straight line of light on the film. Said adjustment may occur by simple visual inspection of the line of light on the film.

Second, the individual adjustment of each photoelectric cell is executed. Said adjustment occurs by connecting the outputs of the amplification circuits of the various cells one by one to an oscilloscope and by axially displacing the holder 59 of the corresponding cell until the signal produced on the screen of the scope as a consequence of the oscillation of the grating 33 becomes minimum. This points thereto that the concerned photocell covers a whole number of periods of the grating so that movement of said grating does not cause any variation in the amount of radiation transmitted to the photocell. Occasional small ripple on the output signal of a cell may be caused by inaccuracies in the pattern of the grating, by movement of the grating in a plane or in planes other than that or those for which the axial adjustment of the photocells was made, etc.

The output signals of the amplifiers of the various photocells may be filtered, clipped, summed, discriminated, etc. in order to produce an indication of the type and the seriousness of a defect that is being detected. We refer to British Pat. Nos. 1,343,115 and 1,379,593 assigned to the same assignee as in the present application, wherein more details about the electronic aspects of a device for sensing a running web for imperfections are set forth.

The following data illustrate the device described hereinbefore.
Number of photocells: 16
Distance between two adjacent cells: 13.5 mm
Photocell: silicon photodiode SD2024D, marketed by Spectronics, USA
Average value for the angle α: 10°
Angle β: 2.5°
Field length L: 18 mm
Width of the line of radiation on the film: 0.3 mm
Width of the radiation transmitting areas of the grating: 0.5 mm
Width of the radiation intercepting areas of the grating: 0.5 mm
Number of periods of the grating per photocell: 18.
Oscillation amplitude of the grating: 20 mm
Revolutions per second of the motor 53: 5
Low frequency response of the amplifier circuits following each photocell: decrease of 6 db/oct. under 25 Hz.
Frequency band that contained sufficient information for the detection of streaklike and specklike irregularities: from 200 to 300 Hz.

The device according to the present invention is not limited to the embodiments described hereinbefore.

The mounting and the driving of the grating may occur in other ways then described. For instance, the mounting of the grating may occur by replacing the linear ball bearings at both extremities of the grating by leaf springs that are disposed in planes normal to the plane of the film and that run in their rest position parallel with the direction of film movement. One end of each leaf spring may be fitted to one end of the grating 33 and the other end of each leaf spring may be fitted to a stationary point of the device.

Oscillation of the grating may occur by an electromagnet that attracts one leaf spring. The excitation of the electromagnet can be done with an amplified signal from an electromagnetic position transducer. By using positive feedback for the amplifier, one can obtain a self oscillating system, the frequency of which is determined by the mass of the moving parts and the elasticity of the springs. Considering that the mass of the suchlike grating arrangement is less than the grating arrangement of FIGS. 5 and 6 as a consequence of the absence of the masses of the linear ball bearings and the connecting rods, the grating arrangement may be oscillated at a higher frequency than the arrangement of FIGS. 5 and 6 for the same energy input. A higher oscillation frequency implies that the amplitude of the oscillation may be lower yet to obtain the same number of alternative interruptions and transmissions of radiation towards the photocells. Oscillation frequencies of 20 cycles per second, with an amplitude of 10 mm can easily be obtained.

Going further into the movement of the grating arrangements described, it may be seen that the velocity of movement is not constant at all but, on the contrary, that it varies from zero at the extreme lateral positions of the grating, to a maximum at the midway position of the grating. The modulation frequency of the photocell signals varies corresponding and it is clear that at the extreme positions of the grating there is no modulation at all. It is thus possible to calculate for a given web speed and a given oscillation frequency of the grating, the length of streak producing an electric signal that will not be passed through the AC amplifier circuit of a photocell with a given lower cut-off frequency. Such length of a streak will be very limited, not to say only sometimes greater than the dimension of a speck-like defect, and therefore the above consideration is of theoretic interest only.

However, it is yet possible to provide a grating arrangement the various areas of which have a constant frequency of displacement.

A first solution may be formed for instance by a disc mounted for rotation plane-parallel with that of the film and situated between the film and the photocell arrangement 34, thus replacing the grating arrangement 33. The shaft of the disc will be situated aside of one edge of the film. The disc may be made of a transparent material, e.g. glass, onto one surface of which there has been formed a spiral groove in a radiation intercepting material, said groove extending in a great plurality of equally spaced convolutions from the center portion of the disc to the periphery thereof, the radius of the spiral portion of the disc corresponding with the length of the line of radiation on the film. Rotation of the disc at a uniform speed causes the successive radiation transmitting and radiation intercepting areas of the disc to run at a uniform speed through the angular field of the photocells, in a direction parallel with that of the line of radiation on the web. It will be understood that the described arrangement is rather bulky to install, and therefore its use is primarily intended for webs of relative small widths, say a width not exceeding 35 mm.

A second solution may be formed by electro-optical systems such as liquid-crystal devices that respond to electric fields to change from radiation transmitting to radiation absorbing or intercepting. So, the grating arrangement 33 of FIGS. 5 and 6 may be replaced by an elongate liquid-crystal grating that is capable of producing a great plurality of adjacent radiation transmitting and radiation intercepting areas, and that upon appropriate control may be made to shift its pattern in the longitudinal direction of the grating device.

The use of the mentioned type of controlled grating is very attractive, since actual micro etching techniques permit to obtain a high precision of the column-like mini-electrodes that have to be excited and de-energized in succession to produce a running transmission pattern, free of any distortion. Furthermore, suchlike liquid-crystal devices are compatible with integrated circuits as a consequence of their reduced working voltage so that they may directly be controlled by such integrated circuits which may be programmed to produce the desired running grating pattern.

It will be apparent from the foregoing that the expression "grating arrangement" is to be construed very broadly, and it includes the above mentioned first and second "solutions".

In the examples described hereinbefore, the width of the radiation transmitting areas was equal to the width of the radiation intercepting areas. It will be noted that this is not an imperative condition for the proper operation of the device according to the invention since both said widths may differ from each other. The only critical conditions are the following ones: all the periods of the grating must be strictly equal to each other, and the angular field of each photocell must cover a whole number of periods of the grating.

The line of radiation on the film may be produced otherwise than by means of fiber optics. For instance, a series of aligned rod-like lamps may be used, or a section of a spherical lens may be used to focus the light from a single incandescent bulb.

The device according to the invention may also be used to inspect materials in reflection rather than in transmission. In such case, the line of radiation is preferably projected on the material on an area where said material contacts, with its rearside a roller surface, thereby to accurately determine the path of the material.

We claim:

1. A device for detecting speck-and streaklike irregularities in a moving sheet material, comprising
    a source for directing electromagnetic energy across at least a portion of the width of the material,
    a row of stationarily mounted radiation responsive photocells, each having a common predetermined length of field parallel to said row, that are substantially uniformly spaced transversely across the path of the sheet material to receive radiation from said source after modulation of said radiation by the moving sheet material,
    a grating arrangement disposed in the path of the radiation to said photocells and serving to intercept and transmit radiation from linear periodically alternating areas in a direction parallel with the photocell row, and
    means for displacing said grating arrangement to reverse the areas of transmission and interception, the linear periodicity of the grating being equal to 1/X times said field length of a photocell, wherein X is an integer at least equal to 5.

2. A device according to claim 1, wherein X is greater than 10.

3. A device according to claim 1, wherein the grating areas for interception and transmission of radiation have equal widths.

4. A device according to claim 1, wherein said grating arrangement comprises an elongated movable grid that has a plurality of adjacent alternatively radiation intercepting and radiation transmitting areas and that is mounted for limited lateral displacement in its own plane, and further including a stationary grid having a plurality of openings corresponding in position with the position of the photocells so that the stationary grid acts as a diaphragm limiting the field length of each photocell to a whole number of periods of said movable grid, and means for oscillating said movable grid over a distance that is at least equal to the length of one period of said movable grid.

5. A device according to claim 4, wherein the frequency of oscillation of said movable grid is at least 5 cycles per second.

6. A device according to claim 1, wherein said photocells are arranged for limited displacement in a direction normal to the plane of the stationary grid, thereby to permit the field length of each cell to be individually adjusted to correspond with a whole number of periods of said grating arrangement.

7. A device according to claim 1, wherein said source of electromagnetic energy is arranged for producing a line of radiation on the sheet material.

8. A device according to claim 1, wherein said photocells are so arranged that they cover overlapping zones on the sheet material.

9. A method of testing sheet material to detect the presence or location of speck- and streaklike irregularities therein affecting radiation transmitting or reflecting properties thereof, comprising the steps of advancing the sheet material in its own plane across a projected path of radiation which intersects the plane of the sheet material at a zone extending in at least one direction in said plane, periodically alternately intercepting radiation transmitted through or reflected from alternating different portions of each of a number of like incremental sub-zones extending in succession along said zone of intersection, detecting the resulting transmitted or reflected modulated radiation by a plurality of photocells each of which has a detection field having a dimension measured parallel to said zone direction equal to a whole number multiple of one of said incremental sub-zones, and deriving AC modulated signals from the output of said cells.

10. A method according to claim 9, wherein said intersection zone has the form of a line.

11. A method according to claim 10, wherein said line is perpendicular to the direction of advancement of the sheet material.

* * * * *